United States Patent
Landau

(10) Patent No.: US 6,607,510 B2
(45) Date of Patent: Aug. 19, 2003

(54) DISPOSABLE NEEDLE-FREE INJECTION APPARATUS AND METHOD

(75) Inventor: Sergio Landau, Laguna Niguel, CA (US)

(73) Assignee: Bioject Medical Technologies Inc., Portland, OR (US)

( * ) Notice: Subject to any disclaimer, the term of this patent is extended or adjusted under 35 U.S.C. 154(b) by 0 days.

(21) Appl. No.: 10/008,563

(22) Filed: Nov. 9, 2001

(65) Prior Publication Data

US 2003/0093030 A1 May 15, 2003

(51) Int. Cl.$^7$ .............................................. A61M 37/00
(52) U.S. Cl. ........................................ 604/140; 604/187
(58) Field of Search ............................ 604/68–72, 118, 604/131, 140–141, 143, 148, 167.01–167.03, 207, 218, 232, 236–238, 246, 249

(56) References Cited

U.S. PATENT DOCUMENTS

| | | |
|---|---|---|
| 2,545,017 A | 3/1951 | Billingsley |
| 2,653,602 A | 9/1953 | Smoot |
| 2,667,874 A | 2/1954 | Dickinson, Jr. |
| 2,680,439 A | 6/1954 | Sutermeister |
| 3,110,309 A | 11/1963 | Higgins |
| 3,115,133 A | 12/1963 | Morando |
| 3,292,621 A | 12/1966 | Banker |
| 3,561,443 A | 2/1971 | Banker |
| 3,688,765 A | 9/1972 | Gasaway |
| 3,695,266 A | 10/1972 | Lussier |
| 3,714,943 A | 2/1973 | Yanof et al. |
| 3,853,125 A | 12/1974 | Clark et al. |
| 3,945,379 A | 3/1976 | Pritz et al. |
| 4,059,107 A | 11/1977 | Iriguchi et al. |
| 4,124,024 A | 11/1978 | Schwebel et al. |
| 4,596,556 A | 6/1986 | Morrow et al. |
| 4,680,027 A | 7/1987 | Parsons et al. |
| 4,717,384 A | 1/1988 | Waldeisen |
| 4,790,824 A | 12/1988 | Morrow et al. |
| 4,913,699 A | 4/1990 | Parsons |
| 4,940,460 A | 7/1990 | Casey et al. |
| 5,009,637 A | 4/1991 | Newman et al. |
| 5,024,656 A | 6/1991 | Gasaway et al. |
| 5,383,851 A | 1/1995 | McKinnon, Jr. et al. |
| 5,503,627 A | 4/1996 | McKinnon et al. |
| 5,730,723 A | 3/1998 | Castellano et al. |
| 5,891,085 A * | 4/1999 | Lilley et al. .................. 604/68 |
| 5,993,412 A | 11/1999 | Deily et al. |
| 6,096,002 A | 8/2000 | Landau |
| 6,132,395 A | 10/2000 | Landau et al. |
| 6,210,359 B1 | 4/2001 | Patel et al. |
| 6,224,567 B1 | 5/2001 | Roser |
| 6,264,629 B1 | 7/2001 | Landau |

FOREIGN PATENT DOCUMENTS

| | | |
|---|---|---|
| WO | WO98/52632 | 11/1998 |
| WO | WO00/33899 | 6/2000 |
| WO | WO00/48654 | 8/2000 |
| WO | WO01/13975 | 3/2001 |
| WO | WO01/13977 | 3/2001 |
| WO | WO01/74425 | 10/2001 |

* cited by examiner

Primary Examiner—Michael J. Hayes
Assistant Examiner—Kevin C. Sirmons
(74) Attorney, Agent, or Firm—Kolisch Hartwell, P.C.

(57) ABSTRACT

In accordance with the current invention, a needle-free injection system includes a cap that has a first seal for sealing an injection orifice when the cap is engaged with an injection end of the system. The cap also includes a push-rod for facilitating priming of the system when engaged with a priming end of the system. The system also includes a push-rod engaging mechanism disposed at the priming end of the system for receiving the push-rod for priming the system. The system further includes a gas cylinder for supplying pressurized gas for injecting, via the injection orifice, an injectate initially disposed within a storage chamber, and a sealing system for preventing the pressurized gas from ejecting the injectate from the system prior to actuation of the system. Actuation of the system is achieved via a slidable trigger plate.

39 Claims, 6 Drawing Sheets

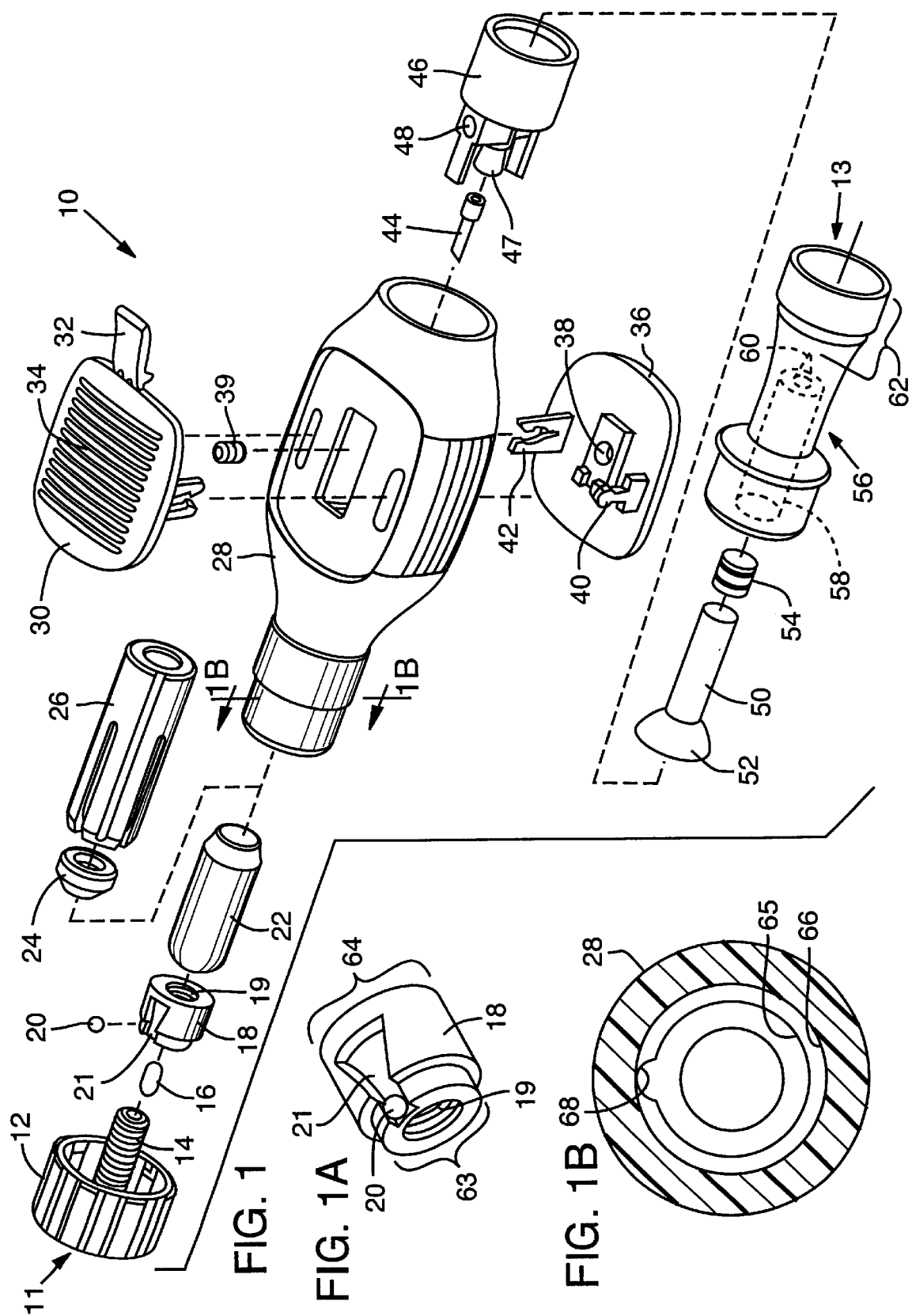

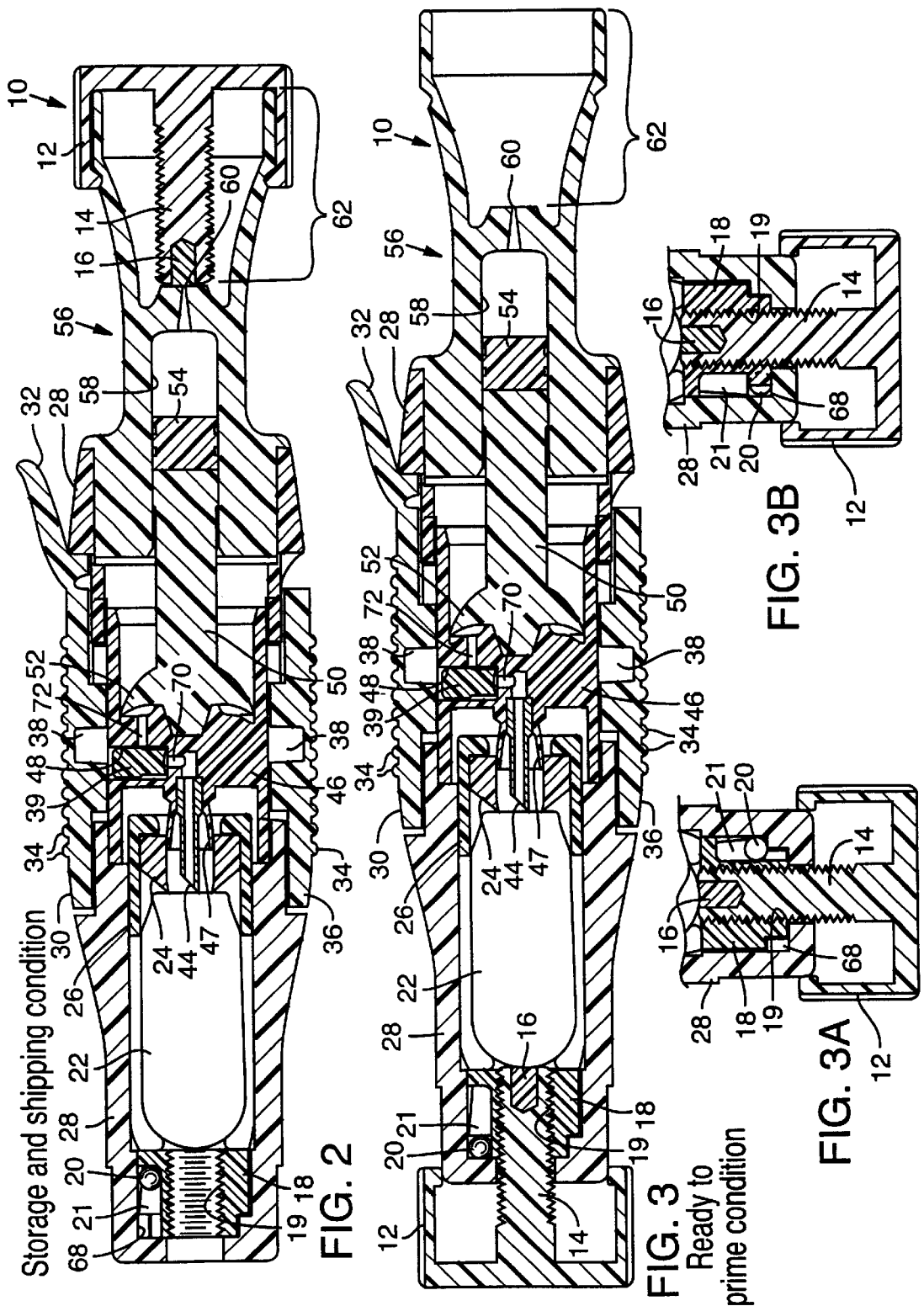

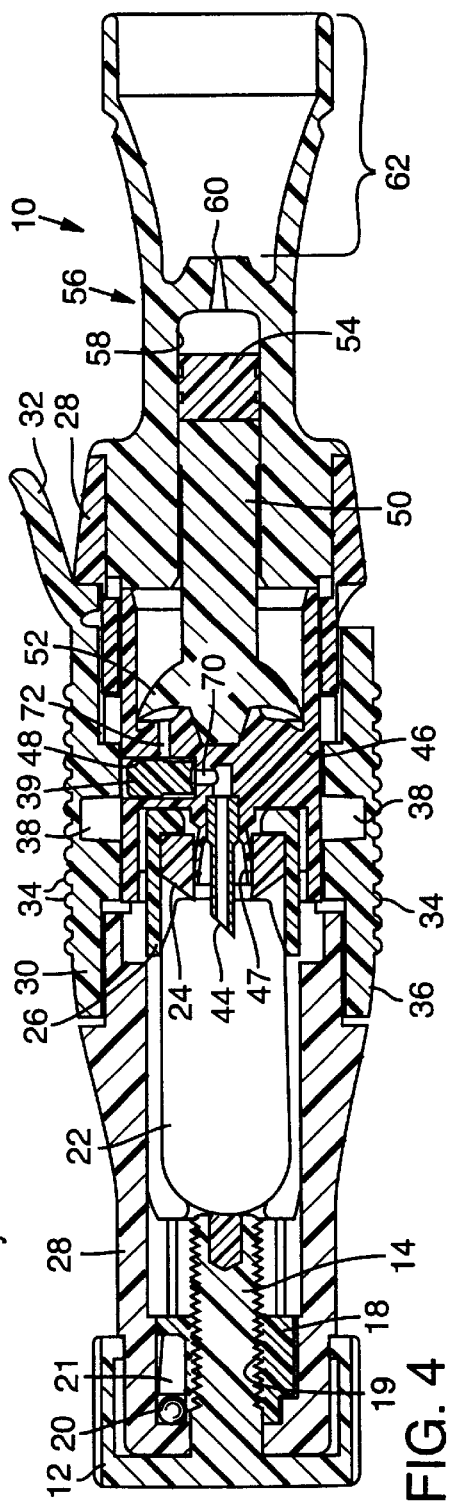

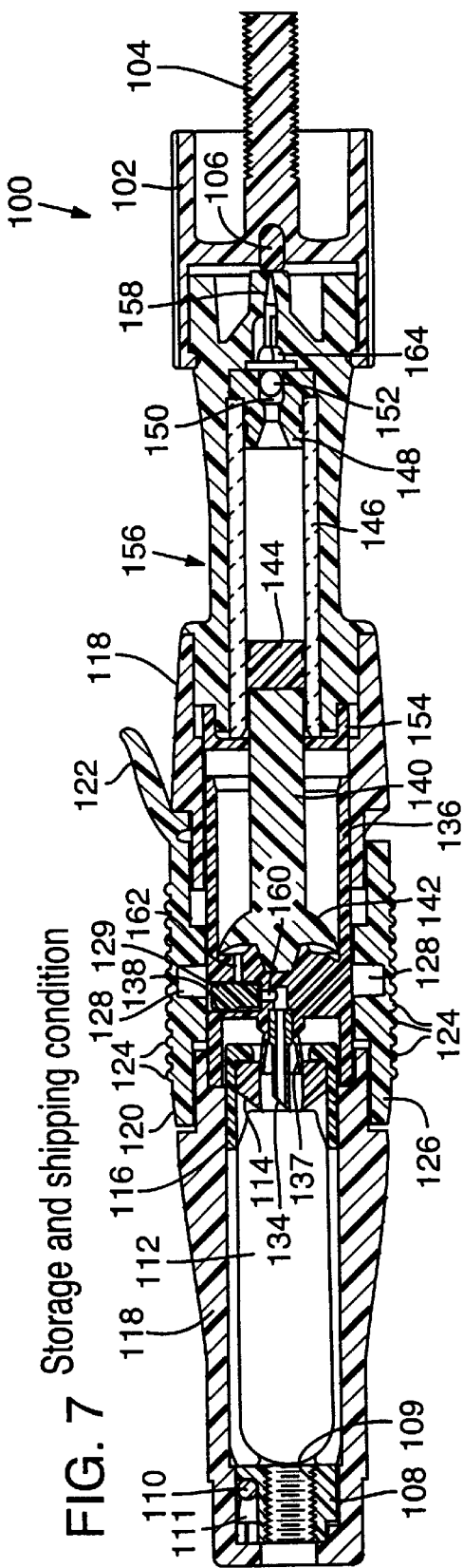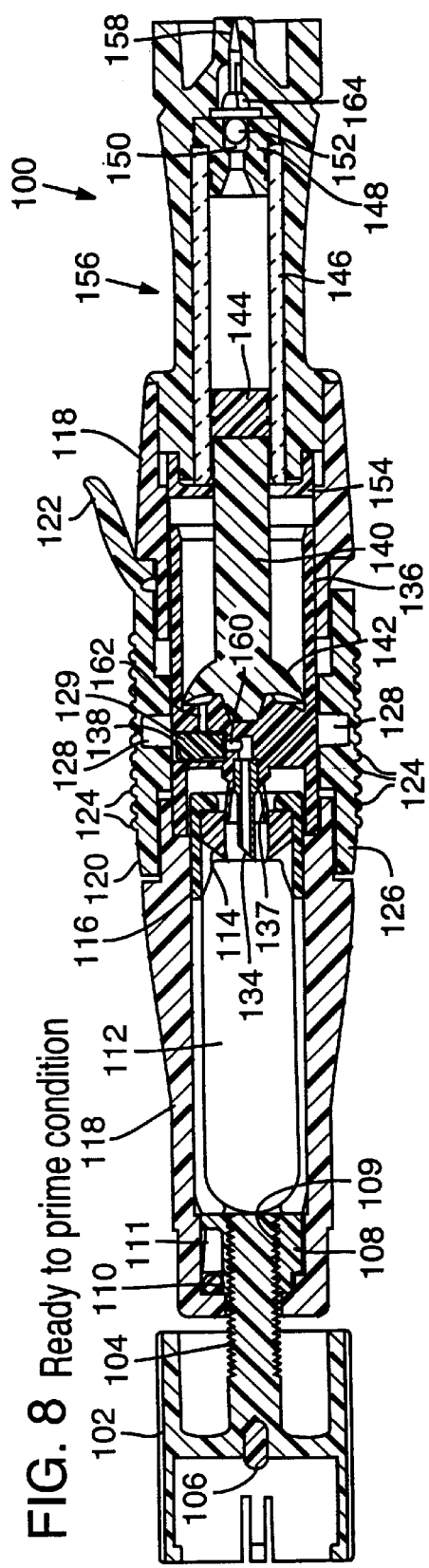
FIG. 7 Storage and shipping condition
FIG. 8 Ready to prime condition

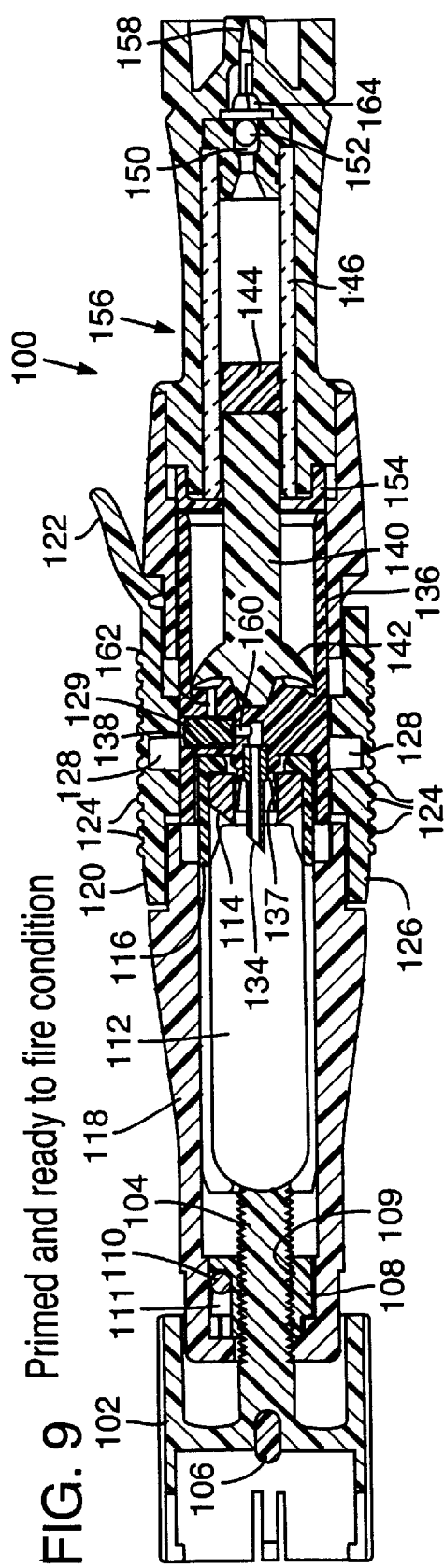
FIG. 9 Primed and ready to fire condition
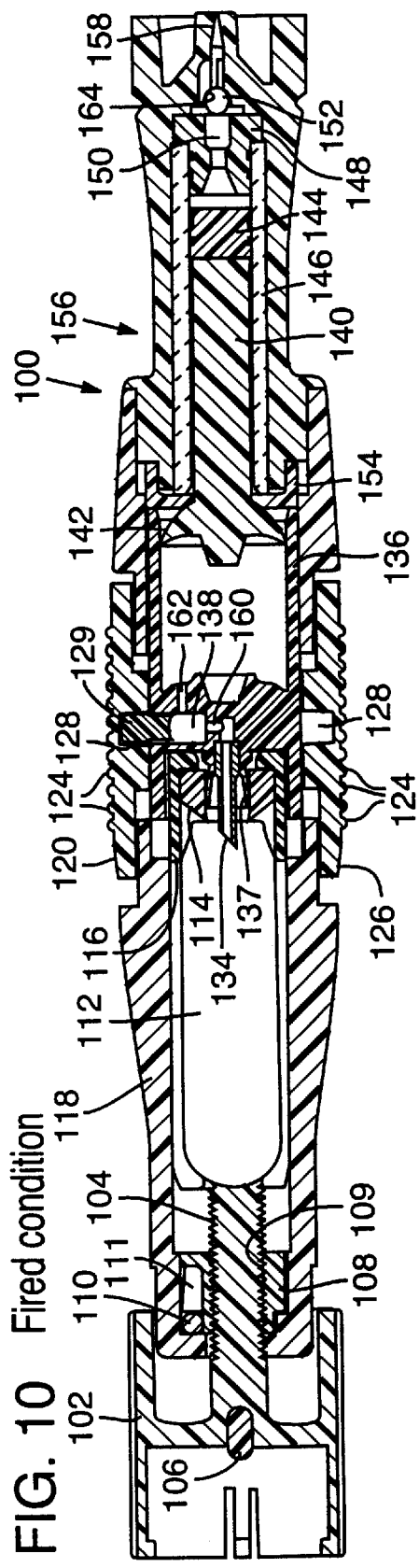
FIG. 10 Fired condition

DISPOSABLE NEEDLE-FREE INJECTION APPARATUS AND METHOD

BACKGROUND OF THE INVENTION

The present invention relates generally to needle-free or needleless injection systems and more specifically to such a system that is particularly well suited for being used a single time and then being discarded.

RELATED TECHNOLOGY

Needle-free systems have been in use for many years. Some such systems have used a pressurized gas to power a hypodermic jet injection. The related technology includes a number of teachings for gas-powered injection devices, including: U.S. Pat. No. 4,596,556 to Morrow, et al.; U.S. Pat. No. 4,913,699 to Parsons; U.S. Pat. No. 5,730,723 to Castellano, et al.; and WIPO publication WO 97/3705 naming Weston and Thornlea as inventors.

SUMMARY OF THE INVENTION

In accordance with the current invention, a needle-free injection system includes a cap that has a first seal for sealing an injection orifice when the cap is engaged with an injection end of the system. The cap also includes a push-rod for facilitating priming of the system when engaged with a priming end of the system. The system also includes a push-rod engaging mechanism disposed at the priming end of the system for receiving the push-rod for priming the system. The system further includes a gas cylinder for supplying pressurized gas for injecting, via the injection orifice, an injectate initially disposed within a storage chamber, and a sealing system for preventing the pressurized gas from ejecting the injectate from the system prior to actuation of the stem. Actuation of the system is achieved via a slidable trigger plate. The sealing stem includes a second, radially displaceable seal initially disposed within a pressurized gas channel, and a corresponding recess in the slidable trigger plate for receiving the second seal as a result of actuation.

BRIEF DESCRIPTION OF THE DRAWINGS

FIG. 1 is an exploded view of a first embodiment of a needle-free injector according to the present invention that may be used for intradermal injections;

FIG. 1A is an isometric view of a priming bushing and a spherical locking body of the first embodiment as they may be disposed when priming the injector;

FIG. 1B is a sectional view of a housing of the first embodiment taken along line 1B—1B of FIG. 1;

FIG. 2 is a side elevation sectional view of the first embodiment, showing the injector as it would be shipped or stored;

FIG. 3 is a side elevation sectional view of the first embodiment, showing the injector in a ready to prime configuration;

FIG. 3A is an enlarged, fragmentary side elevation sectional view of the first embodiment as depicted in FIG. 2, showing a priming bushing in a first position with the spherical locking body disposed in a forward, non-locking position;

FIG. 3B is an enlarged, fragmentary side elevation sectional view of the first embodiment as shown in FIG. 3, showing the priming bushing in a second position and the locking body disposed in a rearward, locking position;

FIG. 4 is a side elevation sectional view of the first embodiment, showing the unit primed and ready to actuate;

FIG. 5 is a side elevation sectional view of the first embodiment, showing the unit after it has been actuated;

FIG. 7 is a side elevation sectional view of the second embodiment, showing the unit as it would be shipped or stored;

FIG. 8 is a side elevation sectional view of the second embodiment, showing the unit in a ready to prime configuration;

FIG. 9 is a side elevation sectional view of the second embodiment, showing the unit primed and ready to actuate;

FIG. 10 is a side elevation sectional view of the second embodiment, showing the unit after it has been actuated.

DETAILED DESCRIPTION OF THE PREFERRED EMBODIMENTS

Figure 6:
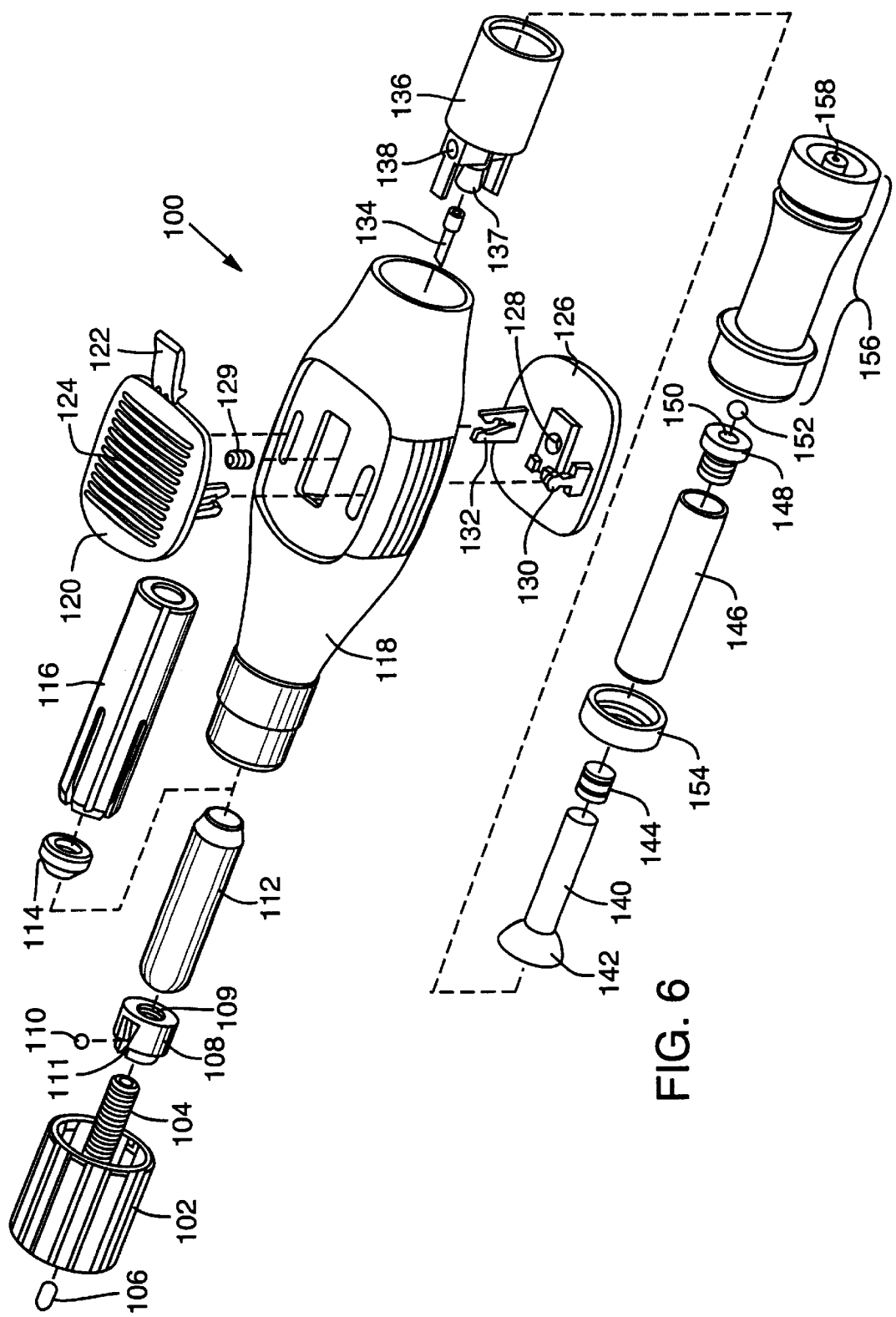
FIG. 6 is an exploded view of a second embodiment of the present invention that may be used for subcutaneous injections.

The objects of the invention are best achieved when the invention takes the form of the embodiments depicted in the figures. FIGS. 1–5 depict a first embodiment of a needle-free injection system, or injector 10, according to the present invention that may be employed for performing intradermal injections. FIGS. 6–10 depict a second embodiment of a needle-free injector 100 according to the present invention that may be employed for performing subcutaneous or intramuscular injections. While these embodiments will be individually discussed as this description continues, it is noted that various aspects of each embodiment may be implemented in intradermal, subcutaneous, or intramuscular injection systems, and the invention is not limited to the particular embodiments shown. Components included in these preferred embodiments are discussed below, while typical operation of these embodiments is discussed in the latter sections of this disclosure.

Construction of the First Embodiment

Referring now to FIG. 1, the various components of needle-free injector 10 are shown in an exploded view. Injector 10 includes injection end 11 and a priming end 13. Injector 10 also includes a cap 12, which initially is positioned at the injector end 11. A push-rod is associated with cap 12, and for this particular embodiment, the push-rod takes the form of threaded member 14, though the invention is not so limited. Alternatively, such a push rod may be unthreaded, may include ratchet grooves or may employ any other number of any surface configurations. For injector 10, an injection orifice seal 16 may be inserted in a distal end of threaded member 14. Cap 12 has multiple purposes, which will be discussed further below. Briefly, however, cap 12 may be employed during shipping and/or storage of injector 10 to seal injector 10 and prevent contamination. Cap 12 may also be employed to prime injector 10, as will be discussed below.

Adjacent the priming end 13, injector 10 may further include a priming bushing 18 and a bushing locking body 20. In the depicted embodiments, locking body 20 is in the form of a spherical ball. Bushing 18 and locking body 20, may cooperate with threaded member 14 when priming injector. Priming of injector 10 will be discussed in further detail below. Briefly, however, FIG. 1A depicts an enlarged isometric view of bushing 18. Bushing 18 includes a first cylindrical portion 63 and a second cylindrical portion 64.

Channel 21 is formed in both cylindrical portions, with portion 64 being larger in diameter than portion 63. Locking body 20 is shown disposed within the portion of channel 21 formed as part of cylindrical portion 63. As may be seen, approximately fifty percent of locking body 20 extends above channel 19. When locking body 20 is disposed within the portion of channel 21 formed in portion 64, locking body 20 would typically not extend above channel 21.

In this regard, FIG. 1B depicts a sectional view of housing along line 1B—1B in FIG. 1. As shown in the drawing, housing 28 includes an inner wall 65 and an outer wall 66. These walls have circumferences that correspond, respectively, with portions 63 and 64 of bushing 18, and are adapted to receive bushing 18. Slot 68 is formed in inner wall 65 of housing 28, and may cooperate with slot 21 of bushing 18 in fixing bushing 18 with housing 28 during priming. These features are discussed in further detail below with respect to FIGS. 3A and 3B.

Referring again to FIG. 1, injector 10 may also include a gas cylinder 22, a gas seal 24, both of which may be inserted into sleeve 26 and work cooperatively in providing pressurized gas for performing injections with injector 10. In this regard, sleeve 26 may precisely position gas cartridge 22 and gas seal 24 with respect to the other components of injector 10 to facilitate priming and actuation of the injector. As indicated in FIG. 1, bushing 18, locking body 20, gas cylinder 22, gas seal 24 and sleeve 26 may be inserted into a housing 28 when assembling injector 10.

Housing 28 may receive a slidable trigger plate 30, which may be used to actuate injector 10 after priming, as will be discussed below. In this respect, trigger plate 30 includes tab 32 that may prevent inadvertent actuation of injector 10 until desired for injection of a user. As is shown in FIG. 1, trigger plate 30 may include corrugations 34 to facilitate sliding of trigger plate 30 when actuating injector 10. A second trigger plate 36 may also be included. For this embodiment, trigger plates 30 and 36 may include a recess 38, which is adapted to at least partially receive gas channel seal 39 as a result of actuation of injector 10, as will be discussed in further detail hereafter. Trigger plates 30 and 36 may also include a locking tab 40 and a locking tab receiving structure 42, which may used to couple trigger plate 30 with trigger plate 36 on opposing sides of housing 28, as is indicated in FIG. 1. In such a configuration, trigger plates 30 and 36 would typically move in unison when slid axially to actuate injector 10.

Injector 10 may also include a piercing member 44, and a gas delivery assembly 46, both of which may be received by housing 28. In this embodiment, piercing member 44 may take the form of a hollow needle, though other techniques may exist. Piercing member 44 typically pierces gas cylinder 22 to release pressurized gas, which may then be employed to facilitate injection of a patient by actuating injector 10 via trigger plate 30 and/or 36. A cupped portion 47 of gas delivery assembly 46 may be disposed around piercing member 44. Cupped portion 47 may be flexible so as to expand when pressurized gas is released from gas cylinder 22 when pierced by piercing member 44. Such expansion of cupped portion 47 may facilitate sealing the pressurized gas within injector 10 until actuation. Gas channel seal 39 is typically inserted into gas delivery assembly 46 via opening 48 (see FIG. 1). Additional specifics of this assembly are discussed below. Cupped portion 47 and gas channel seal 39, co-operate to form a gas sealing system 49, which prevents actuation of injector 10 prior to trigger plate 30 being moved to the "fire" position A plunger 50, including a flanged end 52 and plug 54, may also be included in injector 10. Gas delivery assembly 46 may receive flanged end 52, as is indicated in FIG. 1. Plunger 50 and plug 54 may be received by nozzle 56, typically via injectate storage chamber 58. As will be discussed in further below, plug 54 typically cooperates with plunger 50 to eject injectate from storage chamber 58 via injection orifice 60 as a result of actuating injector 10. For the embodiment depicted in FIG. 1, nozzle 56 includes a spacer 62, which makes injector 10 particularly suitable for performing intradermal injections. It is noted that the majority of components of injector 10 (and 100) would typically be fabricated with molded plastic, though the invention is not so limited.

Construction of Second Embodiment

Referring now to FIG. 6, the various components of needle-free injector 100 are shown in an exploded view. Injector 100 includes a cap 102, which has threaded member 104 incorporated on a first side. An injection orifice seal 106 may be disposed on an opposite side of cap 102 from threaded member 104. As was discussed with respect to injector 10, threaded member 14 may operate as a push rod when priming injector 100 and take any number or forms. In similar fashion as with respect to cap 12 of injector 10, cap 102 may be employed during shipping and/or storage of injector 100 to seal the system and prevent contamination. Cap 102 may also be employed to prime injector 100, as will be discussed further below.

The components and features of injector 100 indicated by reference numerals 108–138 correspond with, and are substantially the same as the components and features of injector 10 indicated by reference numerals 18–48 in FIG. 1 and described above. For the purpose of brevity, these components and features will not be described in detail again with regard to FIG. 6.

However, in addition to the differing aspects of cap 102 discussed above, injector 100, illustrated in FIG. 6, differs from injector 10, illustrated in FIG. 1, in the techniques employed for injectate storage and delivery of injectate into a patient. In this regard, plunger 140 contains a flanged end 142 that may be received by gas delivery assembly 136, in a similar manner as previously discussed. Plunger 140 and plug 144, for injector 100, may be received by injectate storage sleeve 146. Storage sleeve 146 typically takes the form of a glass cylinder, though the invention is not limited in this respect. A seal 148 having a channel 150 formed therein may be inserted into a distal end of storage sleeve 146. A valve body 152 may be initially disposed with channel 150 prior to priming of the system for injection of a patient.

Storage cylinder 146, along with seal 148, valve 152, plug 144, plunger 140 and bushing 154 may be received by nozzle 156 when assembling injector 100. In similar fashion as was discussed with respect to nozzle 56 of injector 10, shown in FIG. 1, nozzle 156 includes injection orifice 158, which is formed therein. Additional aspects of the structure and operation of nozzle 156 are discussed below.

Operation of First Embodiment

Typical operation of injector 10 will be discussed with reference to FIGS. 2–5. Referring first to FIG. 2, injector 10 is shown as it may be stored or shipped. In this regard, cap 12 is engaged with spacer 62. In this configuration, injection orifice seal 16 is in physical abutment with injection orifice 60, which may prevent contamination of an injectate disposed within storage chamber 58 as well as loss of the injectate via injection orifice 60. When shipped, injector 10 is in what may be termed, an unprimed state. In this regard, sleeve 26, in which gas cartridge 22 is disposed, and gas delivery assembly 46, are rearwardly disposed within housing 28 and gas cartridge 22 is not yet pierced.

Referring now to FIG. 3, injector 10 is shown in a ready to prime condition. In this respect, threaded member 14 of cap 12 has been threaded into threaded bore 19 of priming bushing 18, and injection orifice seal 16 is in abutment with gas cartridge 22. When locking body 20 is disposed in a forward position in bushing 18, as shown in FIG. 2, and threaded member 14 is rotated with respect to housing 28, frictional forces resulting from the interface between gas cartridge sleeve 26, gas delivery assembly 46 and housing 28 may result in bushing 18 spinning within housing 28, preventing further advance of threaded member 14 through threaded bore 19. By elevating the forward injection end of injector 10 with respect to the rear end thereof, and continuing to rotate cap 12, locking body 20 may be allowed to move into the rearward position as a result of gravitational forces acting on locking body 20.

FIGS. 3A and 3B depict more detailed, fragmentary sectional views of housing 28, bushing 18 and locking body 20, and illustrate the movement of locking body 20 from the forward to the rearward position. FIG. 3A depicts locking body 20 in the forward position, as shown in FIG. 2. In this respect, slot 21 of bushing 18 is not aligned with slot 68 of housing 28. FIG. 3B corresponds with FIG. 3A, and depicts bushing 18 rotated from the depiction of FIG. 3A such that slot 21 of bushing 18 is aligned with slot 68 of housing 28. As a result of gravitational forces, locking body 20 is now disposed in a rearward position within slot 21 in bushing 18 and slot 68 in housing 28. In this situation, further rotation of cap 12 will result in locking body 20 engaging both bushing 18 and housing 28 via respective slots 21 and 68, and positionally fixing bushing 18 with respect to housing 28.

Fixing bushing 18 within housing 28 will then allow threaded member 14 to continue advancing into threaded bore 19, urging gas cartridge 22, gas seal 24 and sleeve 26 forward within housing 28. This forward movement will, in turn, result in forward movement of piercing member 44, gas delivery assembly 46, plunger 50 and plug 54, which will typically result in displacing any air within storage chamber 58, along with a small amount of injectate, effecting priming of injector 10. When such relative movement is effected between gas cartridge 22 and piercing member 44, gas seal 24 is positioned properly against gas cartridge 22 as a result of initially being precisely positioned by chamfered portions of sleeve 26. This forward movement, resulting from advancing threaded member 14 into injector 10, changes the condition of injector 10 from that shown in FIG. 3 to the condition shown in FIG. 4.

Referring now to FIG. 4, injector 10 is shown in a primed and ready to fire condition. In this view, cap 12 is threaded completely into threaded bore 19 in bushing 18. Gas cartridge 22 has been pierced by piercing member 44, allowing pressurized gas to enter a radial gas channel portion 70 within gas delivery assembly 46. As a result of the pressurized gas being released, cupped portion 47 of sealing system 49 may expand and thus prevent the pressurized gas from escaping the injector. The pressurized gas will also exert pressure on gas channel seal 39. Comparing the relative position of gas channel seal 39 in FIGS. 3 and 4 illustrates that, as a result of priming, gas channel seal 39 is moved from a partially rearward position with respective to recess 38 in trigger plate 30 to a position forward of recess 38. Thus, in the configuration shown in FIG. 4, pressurized gas released from gas cartridge 22, once pierced by piercing member 44, will result in gas channel seal 39 being urged upwardly against the underside of trigger plate 30.

In this configuration, pressurized gas is typically retained within injector 10, as it cannot flow into axial gas channel portion 72 or exit gas delivery assembly 46 via opening 48 due to gas channel seal 39 being disposed between radial gas channel portion 70, axial gas channel portion 72 and trigger plate 30. As depicted in FIG. 4, injector 10 is primed and ready to be actuated for injection after removal of tab 32, which will allow trigger plate 30 to be slid forwardly.

Referring now to FIG. 5, injector 10 is shown after actuation. Sliding trigger plate 30 forward results in gas channel seal 39 being urged upward and being received by recess 38 in trigger plate 30. This displacement, in turn, allows pressurized gas to flow through gas delivery assembly 46 via radial gas channel portion 70 and axial gas channel portion 72, and impinge on flanged end 52 of plunger 50. As result, plunger 50 and plug 54 may be urged rapidly forward, causing an injectate disposed within storage chamber 58 to be expelled via injection orifice 60 to effect injection of a patient. As has been previously indicated, spacer 62 makes injector 10 particularly suitable for performing intradermal injections. Thus, injectate expelled from storage chamber 58 in this manner may be used for such intradermal injections.

Operation of Second Embodiment

The operation of injector 100, described above with reference to FIG. 6, will now be described while referring to FIGS. 7–10 which show injector 100, respectively, in a storage and shipping condition; a ready to prime condition; a primed and ready to fire condition; and a fired condition. These conditions correspond with those shown and described for injector 10 with respect to FIGS. 2–5 and are substantially similar in a number of respects. For purposes of brevity, the following discussion notes differences in the operation and structure of injectors 10 and 100, and does not discuss the previously described similar aspects in detail.

FIG. 7 shows injector 100 in the storage condition. As discussed earlier, injection orifice seal 106 is disposed on one side of cap 102 and threaded member 104 is disposed on the opposite side. Because injector 100 is adapted for subcutaneous injections, disposing injection orifice seal 106 on an opposite side of cap 102 from threaded member 104 results in cap 102 being capable of similar functionality as cap 12 of injector 10, such as preventing contamination and facilitating priming. While injector 100 has been described herein as being suitable for subcutaneous injections, it should be understood that it may be possible to adapt the unit for intramuscular injections as well, simply by increasing the size of injection orifice 158.

FIG. 8 shows injector 100 in a ready to prime condition and FIG. 9 shows injector 100 in a primed and ready to fire condition. Because threaded member 104, bushing 108 and locking body 110 function in a substantially similar manner as discussed with respect to FIGS. 1–5, the operation of these components will not be discussed with respect to injector 100.

However, as with injector 10, when locking body 110 fixes bushing 108 with respect to housing 118, threaded member 104 may then advance into threaded bore 109 in bushing 108. This will urge gas cylinder 122, sleeve 116, plunger 140, and plug 144 forward in priming the injector. As is shown in FIG. 9, the forward movement of plug 144 results in valve 152 shifting forward into injection chamber 164. In this situation, injectate may flow through bypass conduits (not shown) and around valve 152 to remove any air from storage cylinder 146 and/or injection chamber 164. In this respect, injectate within storage cylinder 146 is pushed forwardly during priming. As a result of such priming, a small amount of injectate may dribble out of injection orifice 158, but this is desired to ensure that air has been removed from storage cylinder 146 and injection chamber 164 prior to the injector being used to inject a patient. It is also noted that employing bushing 108 and locking body 110 may assist in removing air from injector 100 as priming is typically accomplished with injector 100 in a position where the injection is raised with respect to the priming end when such a technique is used. Such an orientation would result in air within storage 146 and injection chamber 164 to rise towards injection orifice 158, allowing for its expulsion from injector 100.

FIG. 10 shows injector 100 with tabs 122 removed in a fired condition, after actuation. As with injector 10, actuation of injector 100 may be initiated by sliding trigger plate 120 and/or 126 forward. Pressurized gas from gas cylinder 112 may then displace gas channel seal 129 into recess 128 of trigger plate 120, allowing the pressurized gas to flow though gas delivery assembly 136 via radial gas channel portion 160 and axial gas channel portion 162, and then impinge on flanged end 142 of plunger 140. This impingement may drive plunger 140 and, in turn, plug 144 rapidly forward. This forward movement may then force injectate within storage cylinder 146 to flow around valve 152, through bypass conduits (not shown) and out injection orifice 158 for subcutaneous injection into a patient.

Embodiments of the current invention thus provide apparatus for effective and simple injection, which may be performed by a patient, or other person, using a single hand. This is accomplished using far fewer parts than prior systems. Because this results in the apparatus being relatively inexpensive as compared to prior systems, it may be designed for single use and to be discarded after a single injection.

Of course, variations can be made to the depicted embodiments without departing from the scope of the invention, and the following claims are intended to cover all such variations.

I claim:

1. A needle-free injection system comprising:
   a cap including a first seal for sealing an injection orifice when engaged with an injection end of the system and a push-rod for facilitating priming of the system when engaged with a priming end of the system;
   a push-rod engaging mechanism disposed at the priming end of the system for receiving the push-rod;
   a gas cylinder for supplying pressurized gas for injecting, via the injection orifice, an injectate initially disposed within a storage chamber; and
   a sealing system for preventing the pressurized gas from ejecting the injectate from the system prior to actuation of the system via a slidable trigger plate, wherein the sealing system includes a second, radially displaceable seal disposed in a pressurized gas channel, and a corresponding recess in the slidable trigger plate for receiving the second seal as a result of actuation.

2. The system of claim 1, further comprising an intradermal spacer disposed forward of the injection orifice.

3. The system of claim 2, wherein the first seal is disposed at a distal end of the push-rod.

4. The system of claim 1, wherein the first seal is disposed within a recessed portion of the cap and the push-rod is disposed on an opposite side of the cap from the first seal.

5. The system of claim 1, further comprising an axially movable plunger for urging the injectate forward toward the injection orifice as a result of at least one of priming and actuating the system.

6. The system of claim 1, wherein the gas channel includes a cupped portion, a radial portion, and an axial portion, the second seal being disposed between the radial and axial portions prior to actuation of the system.

7. The system of claim 6, wherein the cupped portion is flexible and expands as a result of pressurized gas being released from the gas cylinder to prevent the pressurized gas from escaping the injector prior to actuation.

8. The system of claim 7, wherein the second seal is radially displaced from the gas channel into the recess in the trigger plate as result of actuating the system.

9. The system of claim 1, wherein the slidable trigger plate includes a removable tab to prevent actuation of the system prior to injection.

10. The system of claim 9, wherein the tab is coupled with the slidable trigger plate via a thinned section, which facilitates removal of the tab prior to injection.

11. The system of claim 1, wherein the slidable trigger plate includes a corrugated surface to facilitate sliding the plate to actuate the system.

12. The system of claim 1, further comprising a second slidable trigger plate including a recess for receiving the second seal as a result of actuation.

13. The system of claim 12, wherein the first and second trigger plates each include a locking tab and a complementing locking tab receiving structure configured to couple the first trigger plate with the second trigger plate on opposing sides of a housing such that the first and second trigger plates move coincidentally during actuation.

14. The system of claim 1, wherein the injectate storage chamber includes:
   a cartridge for holding the injectate prior to injection, the cartridge having a rear end and a front end;
   a plug mounted at the front end of the cartridge, the plug including an injectate channel; and
   a displaceable valve positioned within the injectate channel prior to priming.

15. The system of claim 14, further comprising a drug chamber for receiving the injectate from the cartridge for injection, wherein the drug chamber has a valve seat designed to receive the valve and bypass conduits defined between the valve and the valve seat therein, which facilitate the flow of injectate around the valve during injection.

16. The system of claim 15, wherein bypass conduits are defined in the valve seat.

17. The system of claim 15, wherein the cartridge is glass; the drug chamber, plug, valve and injection orifice are plastic; and the valve is spherical in configuration.

18. The system of claim 1, wherein the push-rod engaging mechanism is positionally dependent.

19. The system of claim 18, wherein the push-rod and the push-rod engaging mechanism include complementing threads.

20. The system of claim 19, wherein the push-rod engaging mechanism includes:
   a bushing having a first cylindrical portion, a second cylindrical portion, and a first axial slot formed in the first and second cylindrical portions;
   a housing having a tier structure for receiving the bushing, the tier structure having an inner wall;
   a second axial slot formed in the inner wall of the tier structure;

a locking body initially disposed within a portion of the slot formed in the second cylindrical portion of the bushing, wherein the locking body moves into a portion of the first slot formed in the first cylindrical portion of the bushing and the second slot formed in the tier structure as a result of gravitational forces when the injection end of the system is elevated with respect to the priming end of the system and the first and second axial slots are nominally aligned.

21. The system of claim 20, wherein the locking body is spherical in configuration.

22. The system of claim 21, wherein the depth of each of the first and second axially slots is approximately one half of the diameter of the locking body and each slot engages the locking body in fixing the bushing relative to the housing.

23. The system of claim 20, wherein the first and second axial slots are aligned as a result of rotational force being exerted on the push-rod engaging mechanism via the complementing threads.

24. The system of claim 23, wherein the locking body fixes the bushing positionally with respect to the housing by engaging the first and second slots as a result of the rotational force.

25. A needle-free injector comprising:
a cap including a first seal for sealing an injection orifice when engaged with an intradermal spacer disposed at an injection end of the injector, the seal being disposed at a distal end of a push-rod included with the cap for facilitating priming of the injector when engaged with a priming end of the injector;
a push-rod engaging mechanism disposed at the priming end of the injector for receiving the push-rod;
a gas cylinder for supplying pressurized gas for injecting, via the injection orifice, an injectate initially disposed within a storage chamber; and
a sealing system for preventing the pressurized gas from ejecting the injectate from the injector prior to actuation via a slidable trigger plate, wherein the sealing system includes a second, radially displaceable seal disposed in a pressurized gas channel, and a corresponding recess in the slidable trigger plate for receiving the second seal as a result of actuation.

26. The injector of claim 25, wherein the push-rod and push-rod engaging mechanism include complementing threads, and the push-rod engaging mechanism is positionally dependent.

27. The injector of claim 26, wherein the push-rod mechanism includes:
a bushing having a first cylindrical portion, a second cylindrical portion, and a first axial slot formed in the first and second cylindrical portions, wherein the first portion has a diameter that is less than the diameter of the second portion;
a housing having a tier structure for receiving the bushing, the tier structure having an inner wall;
a second axial slot formed in the inner wall of the tier structure;
a locking body initially disposed within a portion of the slot formed in the second cylindrical portion of the bushing, wherein the locking body moves into a portion of the first slot formed in the first cylindrical portion of the bushing and the second slot formed in the tier structure as a result of gravitational forces when the injection end of the system is elevated with respect to the priming end of the system and the first and second axial slots are nominally aligned.

28. The system of claim 27, wherein the first and second axial slots are aligned as a result of rotational force being exerted on the push-rod engaging mechanism via the complementing threads.

29. The system of claim 28, wherein the locking body is cylindrical in configuration and fixes the bushing positionally with respect to the housing by engaging the first and second slots as a result of the rotational force.

30. The injector of claim 25, further comprising a piercing member, which pierces the gas cartridge to allow pressurized gas to enter the gas channel as a result of priming the injector by inserting the push-rod of the cap into the priming end of the injector.

31. The injector of claim 30, further comprising a sleeve configured to position the gas cylinder with respect to the piercing member such that the sleeve, gas cylinder and piercing member move in unison during a first portion of priming and the piercing member pierces the gas cylinder during a second portion of priming.

32. The injector of claim 30, wherein the piercing member is a hollow needle.

33. The injector of claim 25, further comprising:
an axially movable plug disposed within the storage chamber for retaining injectate therein; and
a plunger having a distal end in abutment with the plug and a flanged end in fluid communication with the gas channel, wherein the plunger and plug are disposed forwardly as a result of priming the injector by inserting the push-rod of the cap into the priming end of the injector and are rapidly disposed further forwardly as a result of actuation allowing pressurized gas to impinge on the flanged end of the plunger, causing the injectate to be ejected from the storage chamber via the injection orifice.

34. The injector of claim 25, wherein the gas channel includes a cupped portion, a radial portion, and an axial portion, the second seal being disposed between the radial and axial portions prior to actuation of the injector.

35. The injector of claim 34, wherein the cupped portion is flexible and expands as a result of pressurized gas being released from the gas cylinder to prevent the pressurized gas from escaping the injector prior to actuation.

36. The injector of claim 34, wherein the second seal is radially displaced from the gas channel into the recess in the trigger plate as result of actuating the system.

37. The injector of claim 25, wherein the trigger plate includes a corrugated surface to facilitate sliding of the trigger plate to actuate the injector, and a removable tab to prevent actuation prior to injection, the tab being coupled with the trigger plate via a thinned section, which facilitates removal of the tab prior to actuation.

38. The injector of claim 37, further comprising a second slidable trigger plate including a recess for receiving the second seal as a result of actuation and a corrugated surface.

39. The system of claim 38, wherein the first and second trigger plates each include a locking tab and a complementing locking tab receiving structure configured to couple the first trigger plate with the second trigger plate on opposing sides of a housing such that the first and second trigger plates move coincidentally.

* * * * *